(12) United States Patent
Yang

(10) Patent No.: US 11,185,270 B1
(45) Date of Patent: Nov. 30, 2021

(54) WEARABLE DEVICE AND METHOD FOR MONITORING MUSCLE TENSION AND OTHER PHYSIOLOGICAL DATA

(71) Applicant: Yongwu Yang, Belmont, MA (US)

(72) Inventor: Yongwu Yang, Belmont, MA (US)

(*) Notice: Subject to any disclaimer, the term of this patent is extended or adjusted under 35 U.S.C. 154(b) by 515 days.

(21) Appl. No.: 15/888,009

(22) Filed: Feb. 3, 2018

Related U.S. Application Data

(60) Provisional application No. 62/454,562, filed on Feb. 3, 2017.

(51) Int. Cl.
| | |
|---|---|
| *A61B 5/00* | (2006.01) |
| *A61B 5/22* | (2006.01) |
| *A61B 5/0205* | (2006.01) |
| *A61B 5/11* | (2006.01) |

(52) U.S. Cl.
CPC ........... *A61B 5/224* (2013.01); *A61B 5/0002* (2013.01); *A61B 5/0205* (2013.01); *A61B 5/6831* (2013.01); *A61B 5/7246* (2013.01); *A61B 5/7282* (2013.01); *A61B 5/7405* (2013.01); *A61B 5/746* (2013.01); *A61B 5/11* (2013.01); *A61B 2560/0214* (2013.01)

(58) Field of Classification Search
CPC ............... A61B 5/0488; A61B 5/6804; A61B 2562/0219; A61B 5/0022; A61B 5/486; A61B 5/024; A61B 5/1118; A61B 5/11; A61B 5/7264; A61B 2503/10; A61B 5/224; A61B 5/7246; A61B 5/746; A61B 5/7405; A61B 5/7282; A61B 5/0205; A61B 5/0002; A61B 5/6831; A61B 2560/0214; G06F 3/017; G06F 1/163; G06F 3/014; G06F 3/015; A63B 24/0062; A63B 2220/836; A63B 24/0075; A63B 2024/0009; A63B 2024/0065; A63B 2024/0068; A61L 35/7405; A61L 35/0205; A61L 35/0002
USPC ......... 600/300, 301, 546, 587, 595; 434/155
See application file for complete search history.

(56) References Cited

U.S. PATENT DOCUMENTS

| | | | | |
|---|---|---|---|---|
| 7,478,009 | B2* | 1/2009 | Cabrera | A61B 5/1107 482/6 |
| 8,016,776 | B2* | 9/2011 | Bourget | A61B 5/0002 600/587 |
| 8,167,799 | B2* | 5/2012 | Ronchi | A61B 5/0488 600/301 |
| 8,280,503 | B2* | 10/2012 | Linderman | A61B 5/0488 434/155 |
| 8,500,604 | B2* | 8/2013 | Srinivasan | A63B 24/0006 434/247 |
| 2001/0029343 | A1* | 10/2001 | Seto | A61F 2/54 600/587 |
| 2004/0116784 | A1* | 6/2004 | Gavish | A61B 5/0205 600/300 |

(Continued)

*Primary Examiner* — May A Abouelela
(74) *Attorney, Agent, or Firm* — Michael D. Eisenberg

(57) ABSTRACT

A wearable band configured to fit human limbs receives muscle tension data via sensors housed within the device. The processing circuitry generates statistical models for each physical state of a user and compares the received data with the statistical model. The user is alerted when the processing circuitry detects a change in the data that is outside the predetermined range. The sampling rate of measurements increases when a change is detected to confirm the abnormal data.

20 Claims, 14 Drawing Sheets

(56) References Cited

U.S. PATENT DOCUMENTS

| | | | |
|---|---|---|---|
| 2004/0133081 A1* | 7/2004 | Teller | A61B 5/01 600/300 |
| 2005/0049517 A1* | 3/2005 | Mathew | A61B 5/0488 600/546 |
| 2005/0177059 A1* | 8/2005 | Koivumaa | A61B 5/0488 600/546 |
| 2005/0240087 A1* | 10/2005 | Keenan | A61B 5/0205 600/301 |
| 2006/0184059 A1* | 8/2006 | Jadidi | A61B 5/04015 600/546 |
| 2006/0264730 A1* | 11/2006 | Stivoric | A61B 5/0205 600/390 |
| 2008/0009771 A1* | 1/2008 | Perry | B25J 9/0006 600/587 |
| 2008/0119763 A1* | 5/2008 | Wiener | A61B 5/224 600/587 |
| 2008/0243265 A1* | 10/2008 | Lanier | A61F 2/583 623/24 |
| 2009/0326406 A1* | 12/2009 | Tan | G06F 1/163 600/546 |
| 2010/0130893 A1* | 5/2010 | Sankai | A63B 21/4047 601/5 |
| 2010/0137736 A1* | 6/2010 | Addington | A61B 5/202 600/546 |
| 2011/0118621 A1* | 5/2011 | Chu | A61B 5/0488 600/546 |
| 2011/0118696 A1* | 5/2011 | Eckhoff | A61K 31/192 604/502 |
| 2011/0160549 A1* | 6/2011 | Saroka | A61B 5/00 600/301 |
| 2012/0071732 A1* | 3/2012 | Grey | G06F 19/3481 600/301 |
| 2012/0071792 A1* | 3/2012 | Pfeffer | A61B 5/11 600/587 |
| 2012/0172682 A1* | 7/2012 | Linderman | A61B 5/0476 600/301 |
| 2012/0209134 A1* | 8/2012 | Morita | A61B 5/04012 600/546 |
| 2012/0245439 A1* | 9/2012 | Andre | A61B 5/0022 600/310 |
| 2014/0051942 A1* | 2/2014 | Gillette | A61B 5/0006 600/301 |
| 2014/0135593 A1* | 5/2014 | Jayalth | A61B 5/6805 600/301 |
| 2014/0378872 A1* | 12/2014 | Hong | A61B 5/4815 600/595 |
| 2015/0011913 A1* | 1/2015 | Fuke | A61B 5/1116 600/587 |
| 2015/0150488 A1* | 6/2015 | Ishikawa | A61B 5/6828 600/587 |
| 2015/0223743 A1* | 8/2015 | Pathangay | A61B 5/18 600/301 |
| 2015/0272483 A1* | 10/2015 | Etemad | A61B 5/05 600/409 |
| 2015/0272500 A1* | 10/2015 | Kan-tor | A61B 5/7267 600/301 |
| 2015/0272501 A1* | 10/2015 | Maceachern | A61B 5/0531 600/301 |
| 2015/0313496 A1* | 11/2015 | Connor | A61B 5/0478 600/301 |
| 2015/0366504 A1* | 12/2015 | Connor | A61B 5/6804 600/301 |
| 2016/0038073 A1* | 2/2016 | Brown | A61B 5/4836 600/301 |
| 2016/0058519 A1* | 3/2016 | Herr | A61B 34/10 600/438 |
| 2016/0066836 A1* | 3/2016 | Schneider | A61B 5/4836 600/546 |
| 2016/0073949 A1* | 3/2016 | Grant | A61B 5/6897 600/301 |
| 2016/0106365 A1* | 4/2016 | Choi | A61B 5/0205 600/301 |
| 2016/0120048 A1* | 4/2016 | Seo | A61B 5/6843 600/301 |
| 2016/0150987 A1* | 6/2016 | Kwon | A61B 5/04012 600/476 |
| 2016/0166208 A1* | 6/2016 | Girouard | A61B 5/7264 600/546 |
| 2016/0228640 A1* | 8/2016 | Pindado | G06F 16/24 |
| 2016/0375305 A1* | 12/2016 | Martikka | A63B 60/46 600/546 |
| 2017/0196497 A1* | 7/2017 | Ray | A61B 5/11 |
| 2018/0014748 A1* | 1/2018 | Choi | A61B 5/0536 |

* cited by examiner

WEARABLE DEVICE AND METHOD FOR MONITORING MUSCLE TENSION AND OTHER PHYSIOLOGICAL DATA

CROSS-REFERENCES TO RELATED APPLICATIONS

This application claims priority from U.S. Provisional Application Ser. No. 62/454,562 filed Feb. 3, 2017, which is hereby incorporated herein by reference in its entirety.

FIELD OF THE INVENTION

The present invention relates to a wearable device and method for monitoring and analyzing muscle tension and other physiological data.

BACKGROUND OF THE INVENTION

Among the top 10 leading causes of death in the US, stroke ranks #5. A stroke occurs when the blood supply to part of the brain is suddenly interrupted or when a blood vessel in the brain bursts, spilling blood into the spaces surrounding brain cells. Brain cells die when they no longer receive oxygen and nutrients from the blood or there is sudden bleeding into or around the brain. The symptoms of a stroke include sudden numbness or weakness, especially on one side of the body; sudden confusion or trouble speaking or understanding speech; sudden trouble seeing in one or both eyes; sudden trouble with walking, dizziness, or loss of balance or coordination; or sudden severe headache with no known cause.

There is currently no real time monitoring device to detect onset of a stroke. The present invention addresses such a need because it provides a wearable device to monitor muscle tension and/or physiological parameters such as blood pressure and heartbeat. The device also detects any sudden changes in muscle tension and/or physiological parameters; and any abnormal differences in muscle tension and/or physiological parameters between two sides of the body.

BRIEF SUMMARY OF THE EMBODIMENTS OF THE INVENTION

Figure 1A:
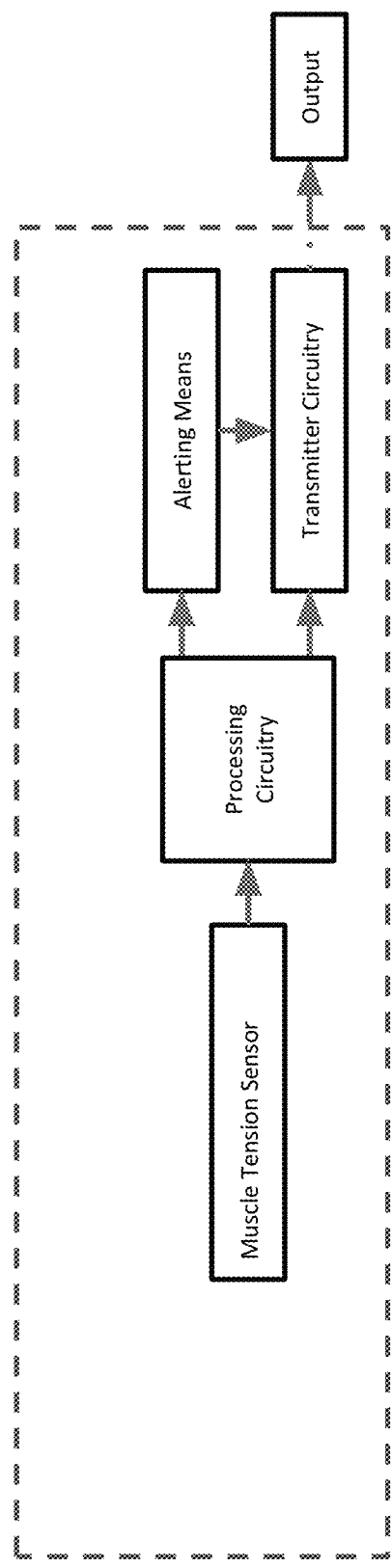
FIG. 1A illustrates a flowchart of a wearable device having a muscle tension sensor, wherein only output is provided.

In a variant, a device for monitoring muscle tension and other physiological data of a user, comprising at least one band adapted to fit human limbs; a first sensor configured to generate muscle tension data; processing circuitry configured to receive and analyze data from the sensor; an alarm component connected to the processing circuitry; transmitter circuitry configured to transmit data to an external device; and a rechargeable battery configured to power the device. The processing circuitry is configured to generate statistical models based on the sensor data and to activate the alarm when a change is detected outside a predetermined range.

In another variant, a second sensor is configured to detect a physical state of the user and to receive physiological data of the user from the first sensor.

In a further variant, the processing circuitry is configured to receive data from the sensor, measured from different limbs of the user, and categorize the data based on a physical state of the user.

In yet another variant, the processing circuitry is configured to compare the data from each sensor to the statistical model generated for each physical state of the user.

In a further variant, the transmitter circuitry of the first device is configured to transmit data to the processing circuitry of the second device.

In yet another variant, the processing circuitry of the second device is configured to compare the data from the first device with the data from the second device and to detect a difference in the data.

In another variant, the alarm component is configured to alert the user when the processing circuitry detects a difference in the data that is outside the predetermined range.

In a further variant, the transmitter circuitry is configured to transmit sound alerts and data to an external device.

In yet another variant, the processing circuitry is configured to continuously update each statistical model with newly received data.

In another variant, each sensor is configured to increase a sampling rate of measurements when the processing circuitry detects a change outside the predetermined range.

In a further variant, an energy-harvesting circuitry is configured to convert energy from an environment of the device to charge the battery.

In yet another variant, a method for monitoring muscle tension and other physiological data of a user, comprising wearing a sensor on a human limb; receiving muscle tension data of a user; analyzing and categorizing the data into a physical state category; comparing the data with a statistical model for the said physical state category; alerting the user when a change is detected outside a predetermined range; and transmitting the data to another device.

In another variant, further comprising receiving physical state or physiological data of the user from the sensor.

In a further variant, further comprising generating a statistical model that corresponds to a physical state of the user.

In yet another variant, further comprising continuously updating a statistical model with recently received data.

In another variant, further comprising wearing a first device on a first limb and a second device on a second limb.

In a further variant, further comprising transmitting data from the first device to the second device.

In yet another variant, further comprising comparing the data of the first device with data of the second device and detecting a change outside of a predetermined range.

In another variant, further comprising increasing a sampling rate of measurements when a change outside of the predetermined range is detected.

DETAILED DESCRIPTION OF THE EMBODIMENTS OF THE INVENTION

In a variant, referring generally to FIGS. 1A-14, a wearable monitoring device comprises a muscle tension sensor, processing circuitry, transmitter circuitry, and an alerting means. The device may also include motion sensors and physiological sensors. The wearable monitoring device is affixed to the user during operation wherein the housing of the device includes a physical size and shape that is suitable to fit the user's limbs and does not hinder user's routine daily life.

Figure 1B:
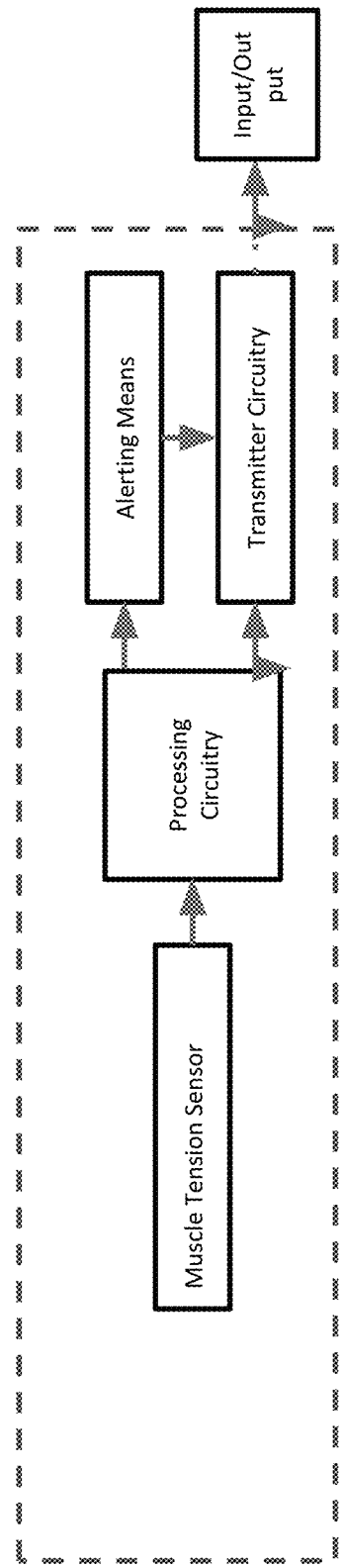
FIG. 1B illustrates a flowchart of a wearable device having a muscle tension sensor, wherein input may be received while output is provided.

In another variant, referring to FIGS. 1A-1B, the device is used alone or in a pair. The muscle tension sensor measures the user's muscle tension. The processing circuitry records, categorizes, and analyzes the muscle tension data and continuously builds dynamic statistical models corresponding to a user's different physical states. By discriminant analysis of the newly acquired muscle tension data against the statistical models, the processing circuitry detects any sudden abnormal changes (a significant increase or decrease from its normal means) and provides a sound signal alerting the user about abnormal changes which needs further attention from medical professionals. The device also outputs the recorded data and analysis results through a transmitter to, for example, an external interface, the internet, or a medical care facility network. FIG. 1B shows an embodiment of the present invention similar to FIG. 1A, but with a two way transmitter circuitry. This embodiment is used in a pair with FIG. 1A, where the pair is worn on either the user's hands or feet. The transmitter in FIG. 1A sends the measured muscle tension data of one hand and/or one foot to the transmitter in FIG. 1B. The processing circuitry in FIG. 1B calculates the difference between the two devices and detects any sudden abnormal differences above a certain threshold. Upon detecting and confirming a sudden abnormal difference, the device will send an alerting signal to the user, and/or transmit the recorded data and analysis results through the transmitter to, for example, an external interface, the internet, or medical care facility network.

In a further variant, the wearable monitoring device of the present invention has an interface or communicates via any connectivity and protocol (for example, wired, wireless, electrical and or optical and/or all types and forms of USB and/or removable memory). All communication mechanisms, techniques, and architectures are intended to fall within the scope of the present invention. Thus, the device may employ wired and/or wireless transmitter circuitry to communicate.

In yet another variant, the processing circuitry employs a decision tree-based technique or algorithm to interpret or assess the changes in muscle tension data instead of a discriminant analysis.

In another variant, the processing circuitry employs filtering methods and state estimation to mitigate, address, and/or alleviate noise and outliers present or inherent in the data.

Figure 2:
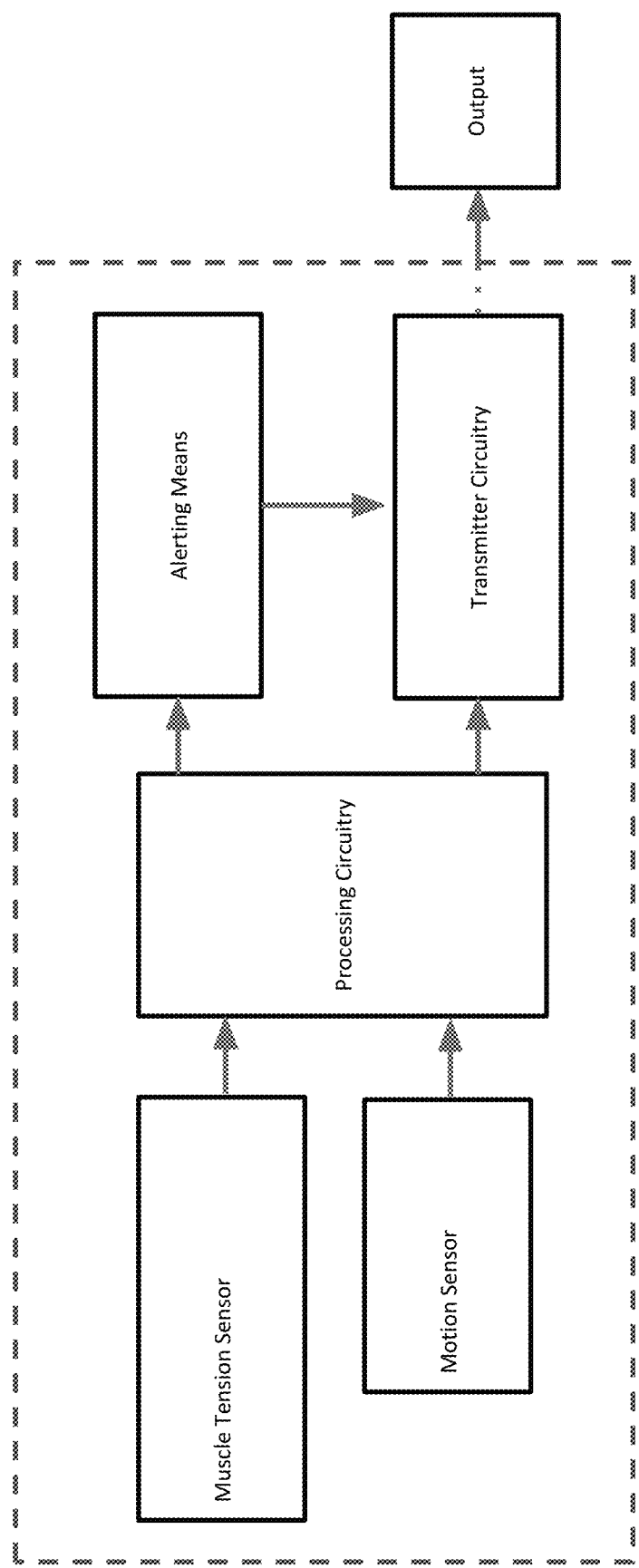
FIG. 2 illustrates a flowchart of a wearable device having a muscle tension sensor and a motion sensor with only an output.

In a further variant, referring to FIG. 2, the device comprises a muscle tension sensor and a motion sensor. Both sensors send their signals to the processing circuitry for processing.

Figure 3A:
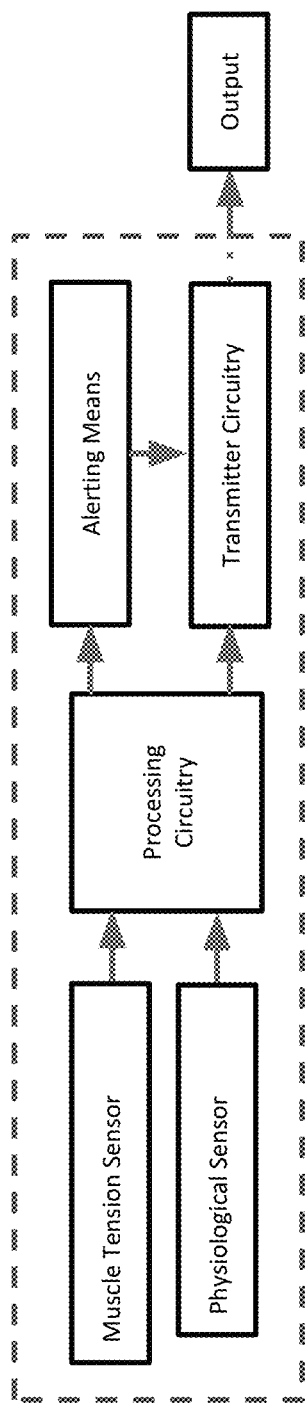
FIG. 3A illustrates a flowchart of a wearable device having a muscle tension sensor and a physiological sensor, wherein only output is sent.
Figure 3B:
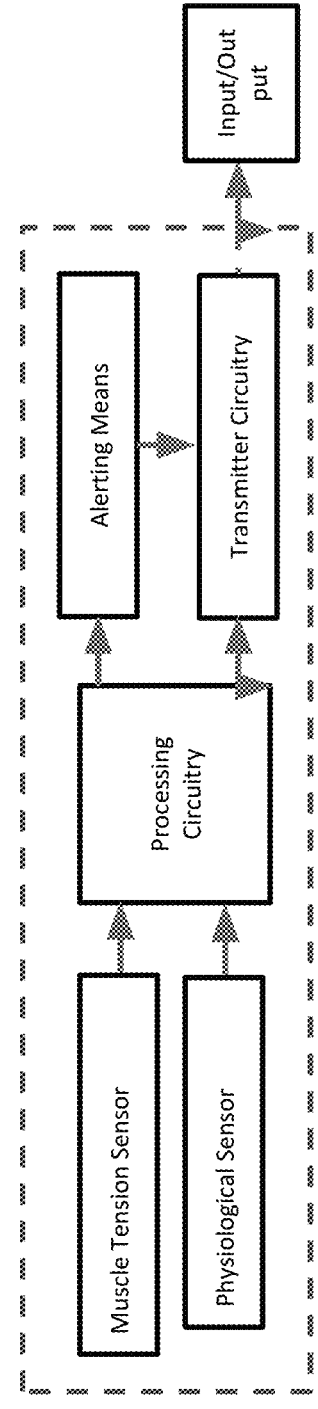
FIG. 3B illustrates a flowchart of a wearable device having a muscle tension sensor and a physiological sensor, wherein input may be received while output is provided.

In yet another variant, referring to FIGS. 3A-3B, the wearable monitoring device includes one or more physiological sensors, in addition to the muscle tension sensor, to further assess the physiological changes of the user. For example, the physiological sensor(s) may analyze blood pressure, heart rate, and/or vein pulse wave data which is representative of the physiological condition of the user. The processing circuitry may correlate the data from the physiological sensor(s) with the muscle tension data to further confirm the onset of abnormal changes of the body, which needs medical attention to avoid any delays. This embodiment can be used alone, or in pair with the embodiment in FIG. 3B. FIG. 3B shows an embodiment of the present invention similar to FIG. 3A but with a 2-way transmitter circuitry.

Figure 4:
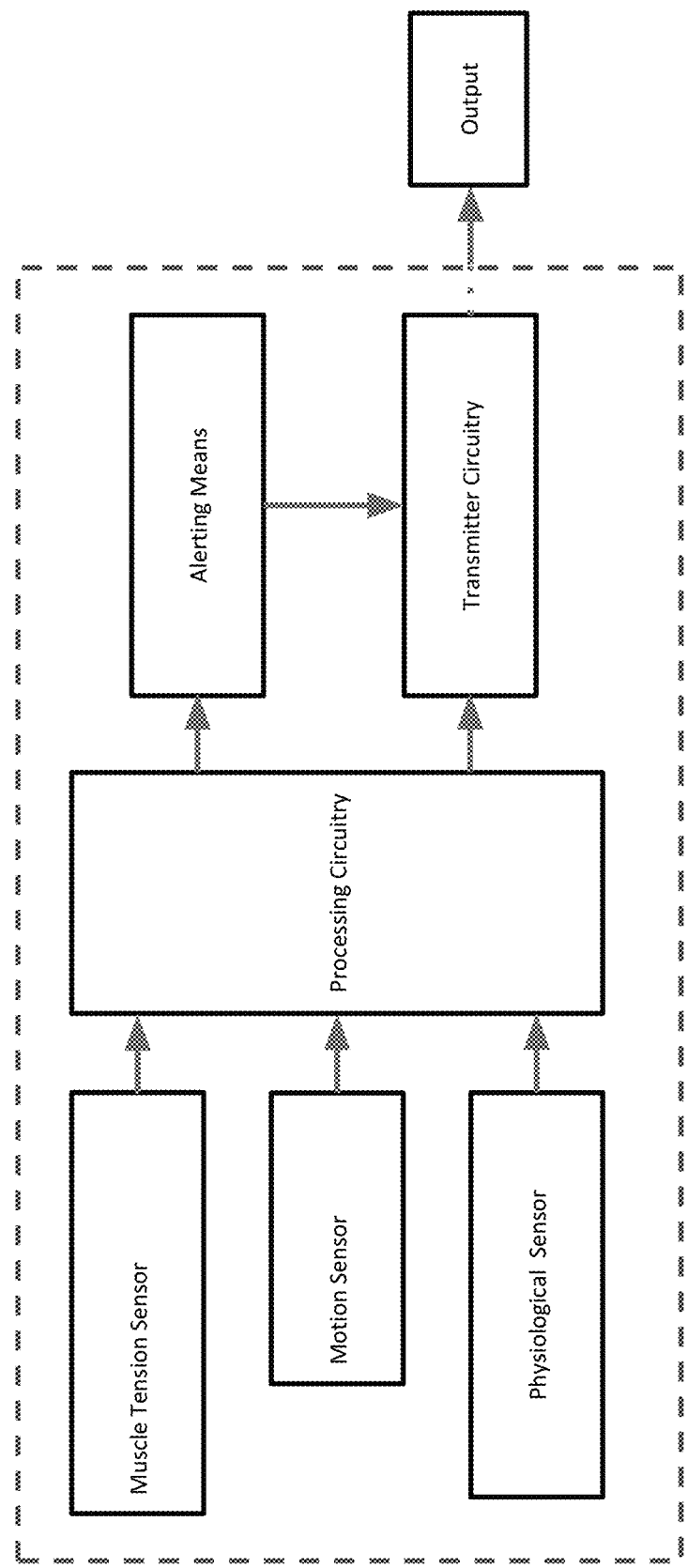
FIG. 4 illustrates a flowchart of a wearable device having a muscle tension sensor, a motion sensor, and a physiological sensor with an output only.

In another variant, referring to FIG. 4, the wearable monitoring device includes a muscle tension sensor, one or more motion sensors, and one or more physiological sensors. In operation, the motion sensor determines the user's physical state. The processing circuitry performs a discriminant analysis of the measured muscle tension data and physiological data according to the statistical model of the determined physical state.

Figure 5:
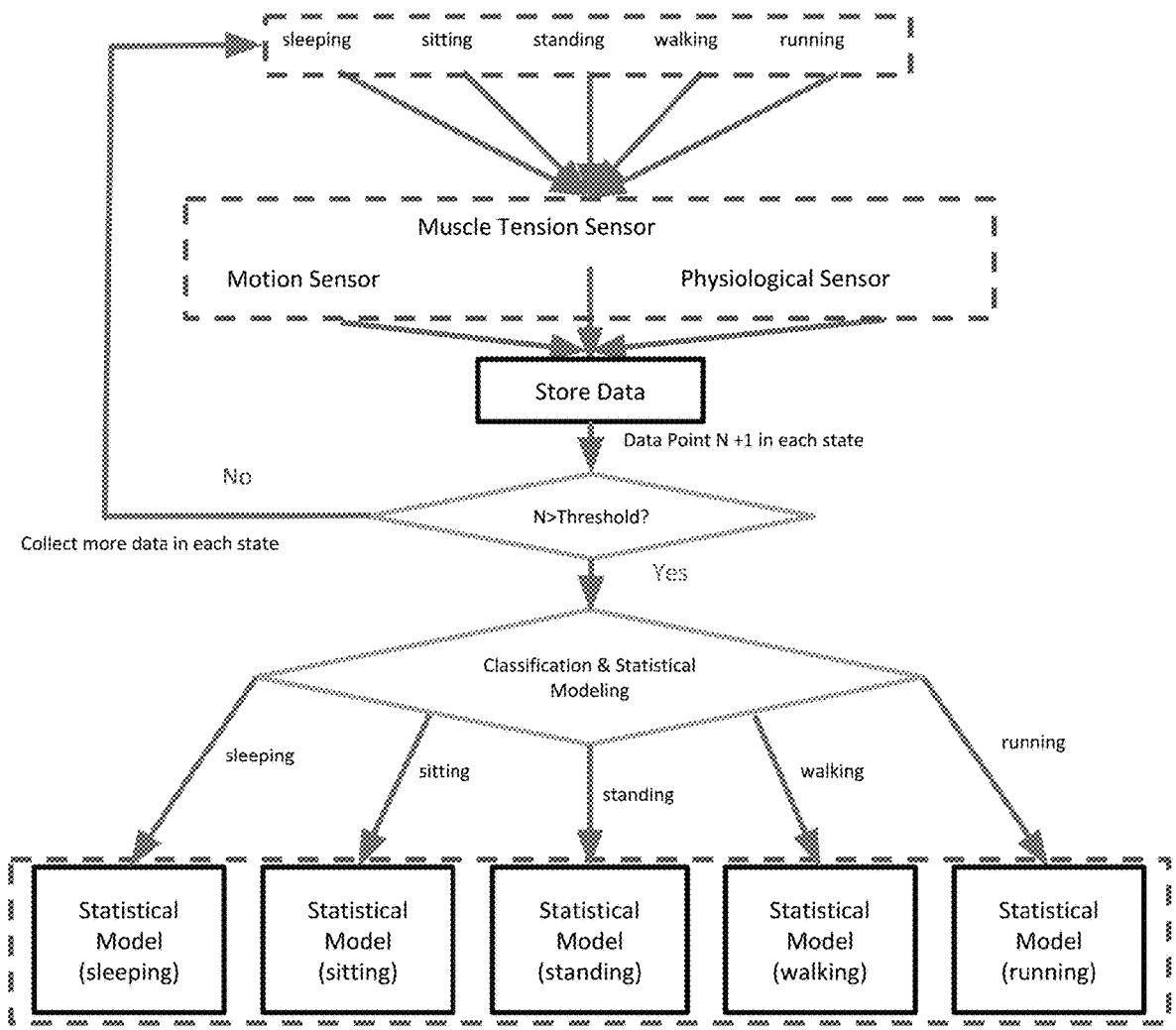
FIG. 5 illustrates a flowchart of device processes for generating statistical models during various physical states.

In a further variant, referring to FIG. 5, the device continuously creates statistical models for the various physical states of the user based on recently received data. The user uses the device to collect muscle tension data, and/or motion data, and/or physiological parameters under all possible physical states including sleeping, sitting, standing, walking, and running. The processing circuitry classifies and builds a statistical model for each physical state which is used for discriminant analysis during real time monitoring. The center of the flowchart in FIG. 5 conveys the sensor data being analyzed for abnormal changes. If the data is equal to or lower than the threshold, then more data is collected in each state to confirm abnormal measurements. If the data is greater than the threshold, then the statistical models are created for various types of physical states, such as sleeping, sitting, standing, walking, and running.

Figure 6:
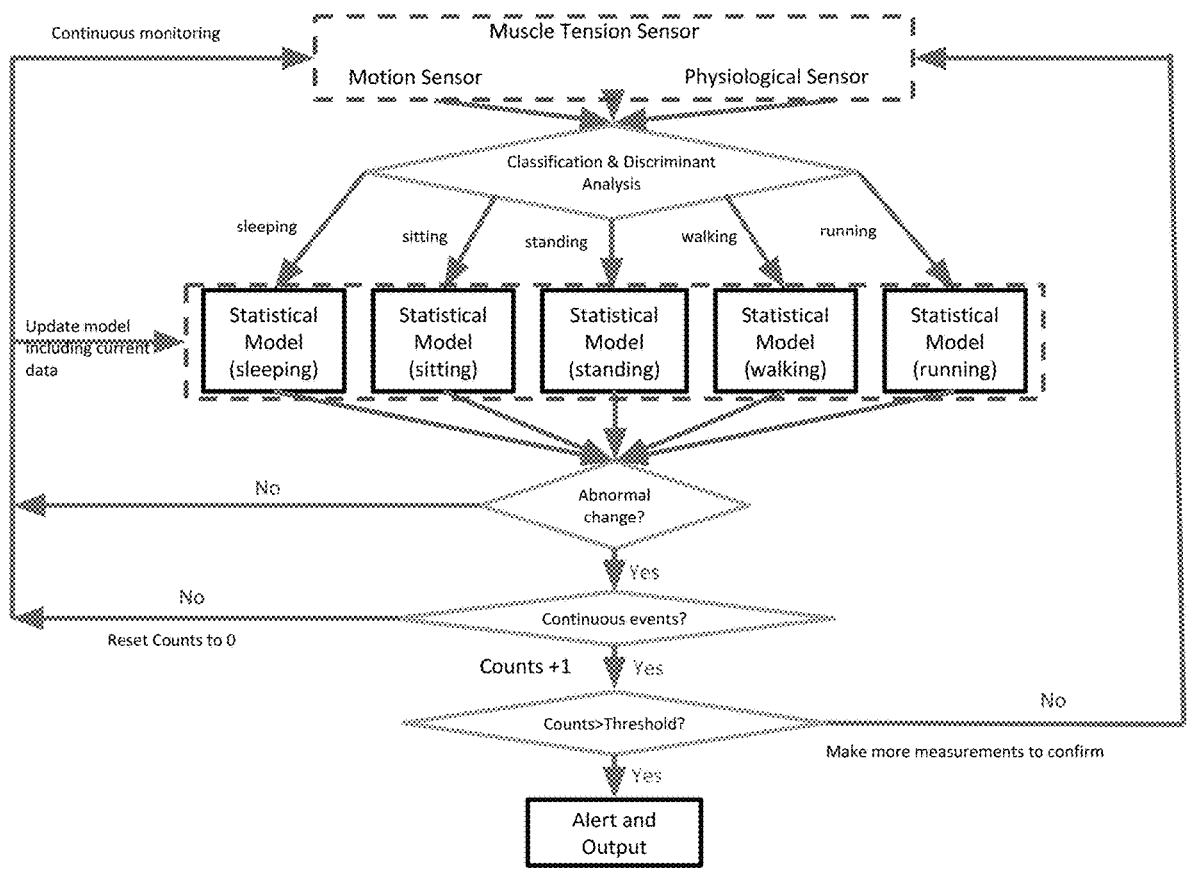
FIG. 6 illustrates a flowchart of device processes for comparing input data to statistical models for each physical state.

In yet another variant, referring to FIG. 6, the device compares input data to statistical models for each physical state. The user wears the device on his hand and/or foot. A sensor monitors user's muscle tension, physical state, and/or physiological parameters, and performs a discriminant analysis against the statistical models to detect possible abnormal changes. Once an abnormal change is detected, the device calculates more measurements to confirm the abnormal changes are real. Once confirmed, the alerting device provides a signal to the user and outputs the recorded data and analysis results to a cell phone, tablet, and/or computer for medical professionals to further analyze the data. The center of the flowchart shows the data being received and compared to the statistical models built previously for each physical state. If there is no abnormal change, monitoring continues regularly. If there is an abnormal change detected, then the device determines whether the abnormal change is continuous. If not, regular monitoring continues. If the abnormal change is continuous, then it makes more measurements to confirm and upon confirmation, alerts the user and outputs the results to an external device. The processing circuitry includes the newly measured normal muscle tension data, motion sensor data, and/or physiological data to update statistical models continuously.

In another variant, the sampling rate of the sensors of the wearable monitoring device may be predetermined or fixed. In one embodiment, the sampling rate is fixed at a lower rate during the normal operation to save power. When an abnormal change is detected, the sampling rate is triggered to increase measurements to confirm the abnormal change is real.

Figure 7:
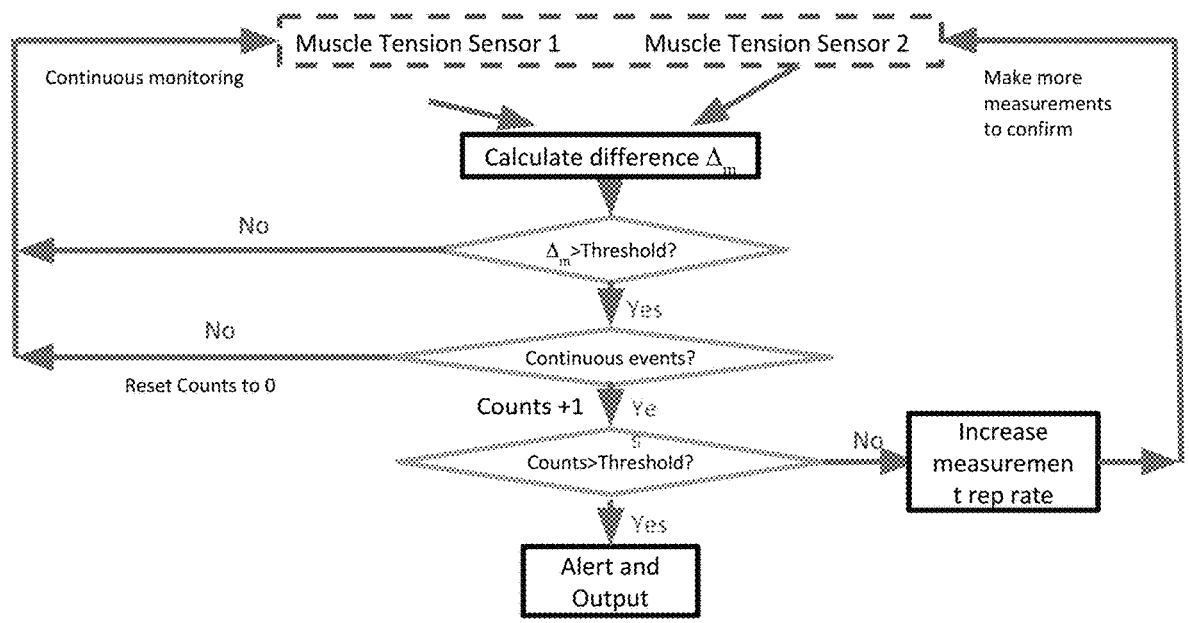
FIG. 7 illustrates a flowchart of analyzing data received from two muscle tension sensors working simultaneously.

In a further variant, referring to FIG. 7, two muscle tension sensors are used simultaneously on either both hands or both feet. In this embodiment, calculation and data analysis may be implemented in the master wearable monitoring device. Here, the slave wearable monitoring device may store and communicate muscle tension data to master monitoring device. The master monitoring device calculates the difference of muscle tension data between the master and slave devices. When the difference is less than the set threshold, the normal monitoring process continues. When the difference exceeds the threshold, the sampling rate is triggered to increase the muscle tension measurements to confirm the abnormal difference is real. Once the abnormal difference is confirmed, the alerting device is triggered to send a signal to the user and/or to output to an external interface for further medical attention. The threshold is continuously updated by incorporating newly calculated normal differences of muscle tension data.

Figure 8:
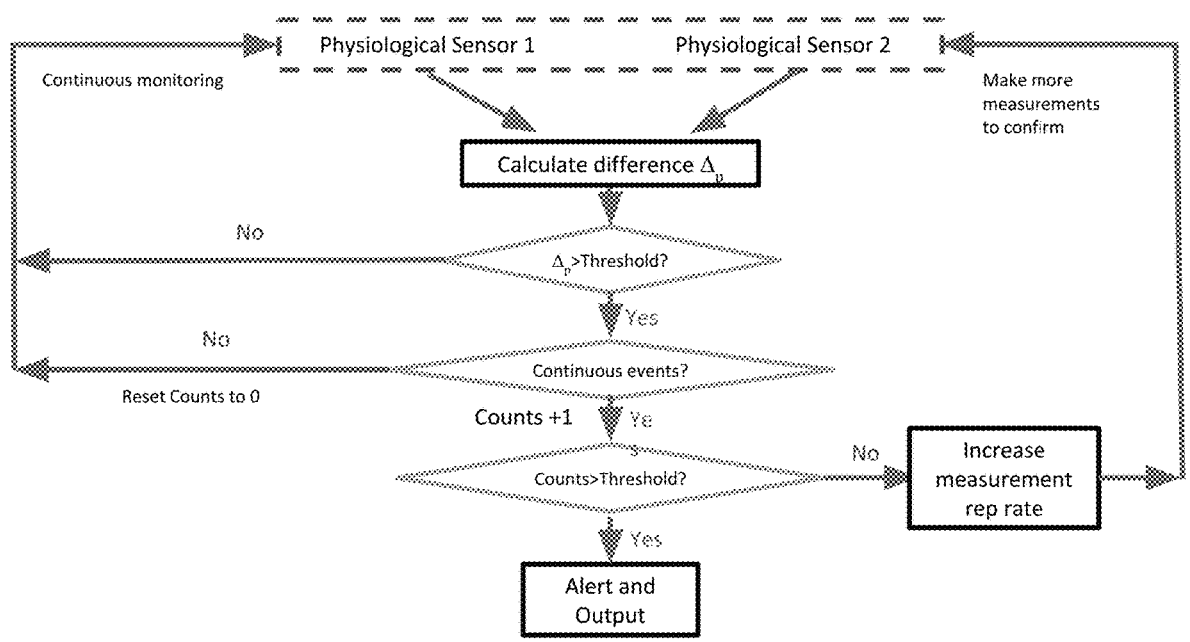
FIG. 8 illustrates a flowchart of analyzing data received from two physiological sensors working simultaneously.

In yet another variant, referring to FIG. 8, two physiological sensors are used simultaneously on both hands or feet. The physiological sensors function in the same way as using two muscle tension sensors simultaneously (FIG. 7).

Figure 9:
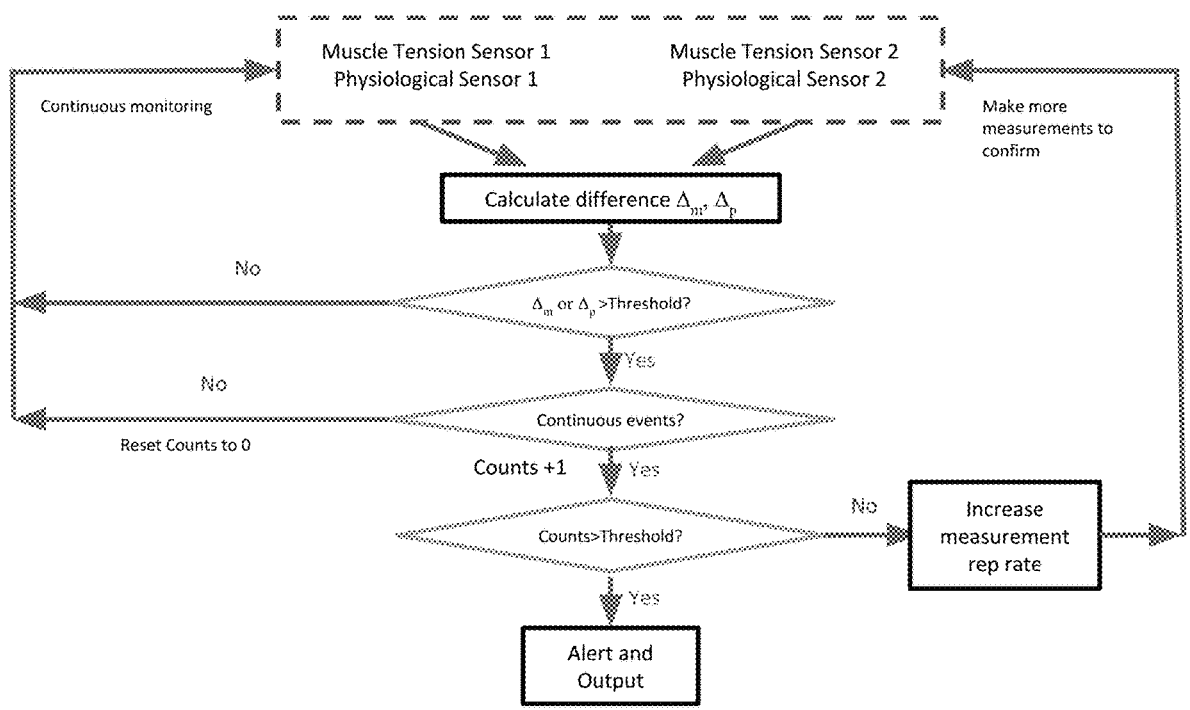
FIG. 9 illustrates a flowchart of analyzing data received from two pairs, each comprising a muscle tension sensor and a physiological sensor, working simultaneously.

In another variant, referring to FIG. 9, two devices including both muscle tension sensors and physiological sensors are used simultaneously on both hands or feet. The pairs of sensors operate in the same way as in the variants depicted in FIGS. 6-7, however here the difference is calculated between the measurements of each pair of sensors. For example, the difference is calculated between muscle tension sensor 1 and muscle tension sensor 2, and the difference is calculated between physiological sensor 1 and physiological sensor 2. Those two measured differences are the results compared against the set threshold and the rest of the flowchart operates in the same way as in the variants depicted in FIGS. 6-7.

In a further variant, the data and parameters derived by the wearable monitoring device may be transferred, displayed, and/or modified remotely as in, for example, a computer program or website, utilizing a wireless network. Such content may furthermore be modified and analyzed by the remote application to build better statistical and discriminant models which may be transferred back to the device for storage and update of the models for better discriminant analysis in the future.

In yet another variant, the wearable monitoring device may also transmit its data to a secondary display device so that the user, caregiver, or doctor may see its output in real-time. The device may include a rechargeable battery or ultracapacitor to provide electrical power to the circuitry and other elements of the device. The energy storage element (for example, battery or ultracapacitor) may obtain energy from a charger.

In another variant, the device includes an active or passive energy-harvesting circuitry wherein the energy acquired, obtained and/or generated by the circuitry is employed to immediately power the device or stored in, for example, a rechargeable battery or ultracapacitor for later use by the rechargeable battery or ultracapacitor. The circuitry acquires energy from signals in the surrounding atmosphere and converts that energy to charge in the battery or ultracapacitor. The energy converted may also be used to supplement the existing charge.

In another variant, the device may be coupled to a bracelet, formed of flexible material.

Figure 10A:
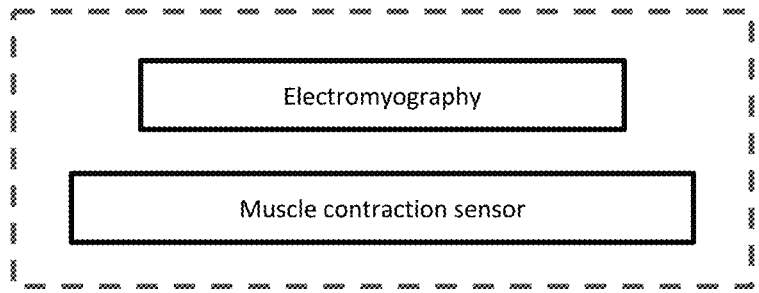
FIG. 10A is a block diagram representation of muscle tension sensors.
Figure 10B:
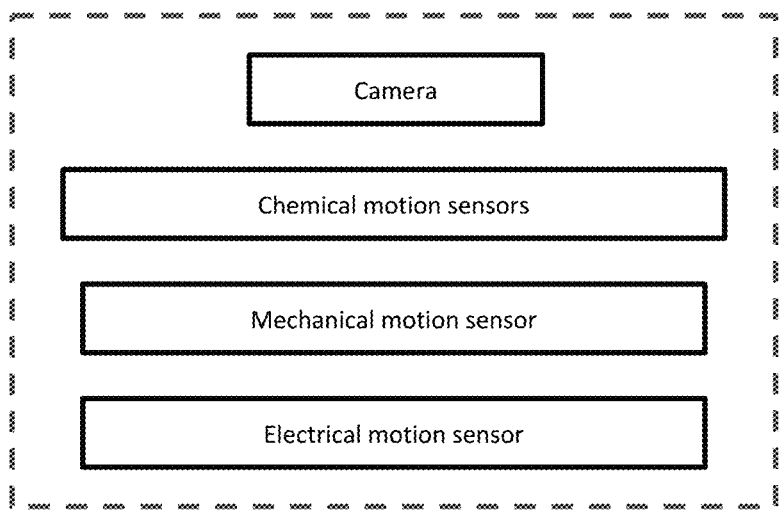
FIG. 10B is a block diagram representation of motion sensors.
Figure 10C:
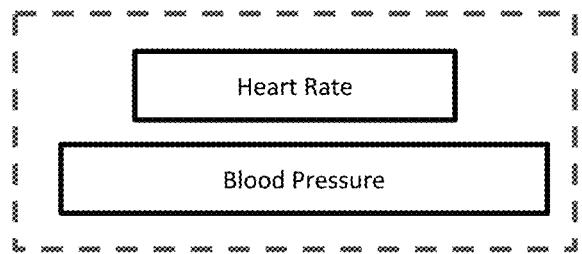
FIG. 10C is a block diagram representation of physiological sensors.

In yet another variant, referring to FIGS. 10A-10C, the wearable monitoring device may include a variety of sensors in addition to the muscle tension sensor. Referring to FIG. 10A, the muscle tension sensor may utilize electromyography (EMG) or a muscle contraction sensor. Referring to FIG. 10B, the motion detector may include a camera or one or more motion sensors. Motion sensors include a chemical motion sensor, electrical motion sensor, or mechanical motion sensor. The camera or motion sensor determines the user's physical states such as sleeping, sitting, standing, walking, and running, thus categorizing measured muscle tension data, which speeds up discriminant analysis and improves efficiency and accuracy. Referring to FIG. 10C, the physiological sensor measures heart rate and/or blood pressure.

Figure 11:
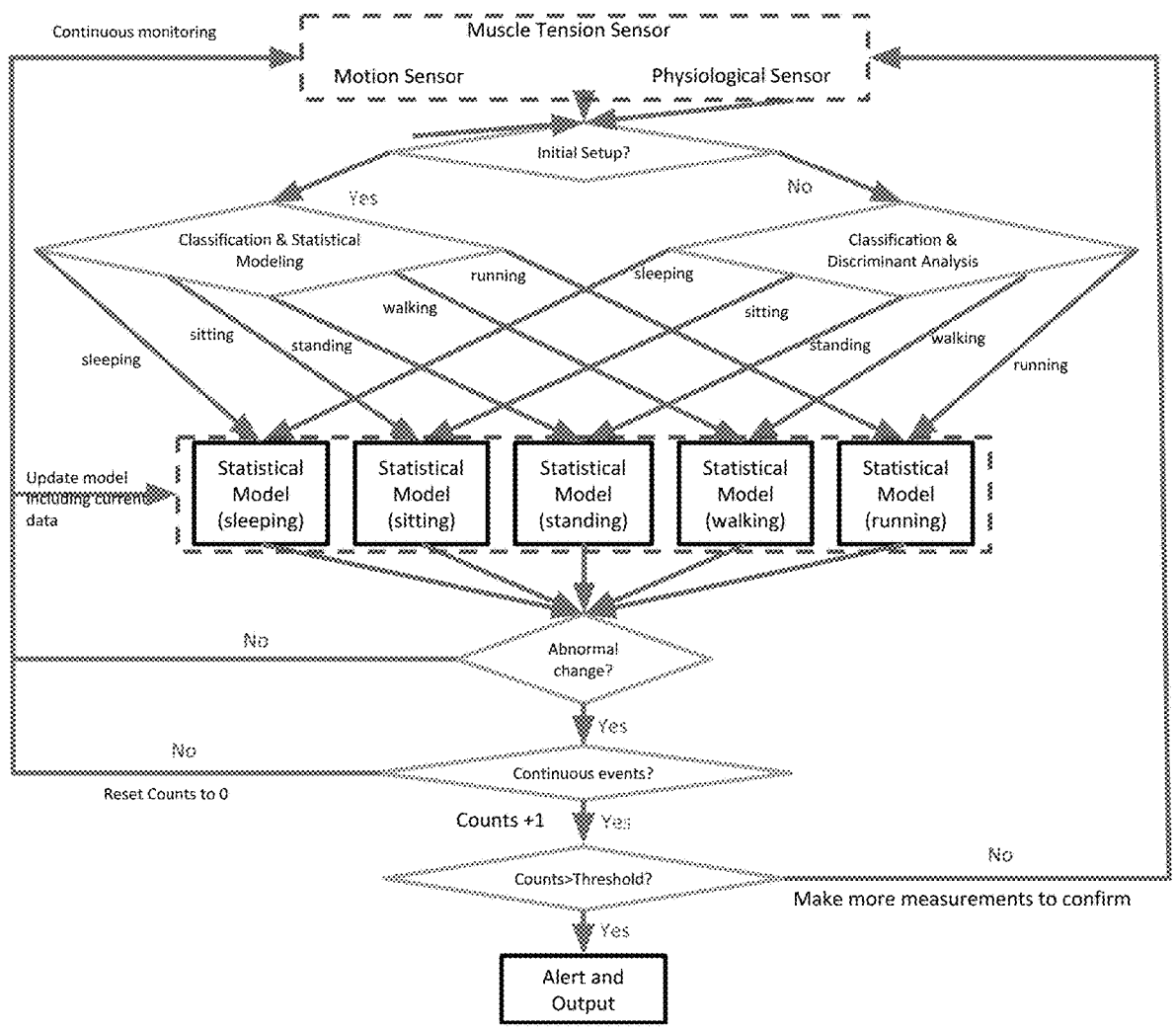
FIG. 11 illustrates a flowchart of device processes.

In another variant, referring to FIG. 11, the device receives input data via its sensors and begins with an initial setup. If there are statistical models in the device, no initial setup is needed, then the device begins the classification and discriminant analysis process. If it is the first time to use the device, there is an initial setup. The device begins to build classification and statistical models with the collected data from sensors.

Figure 12:
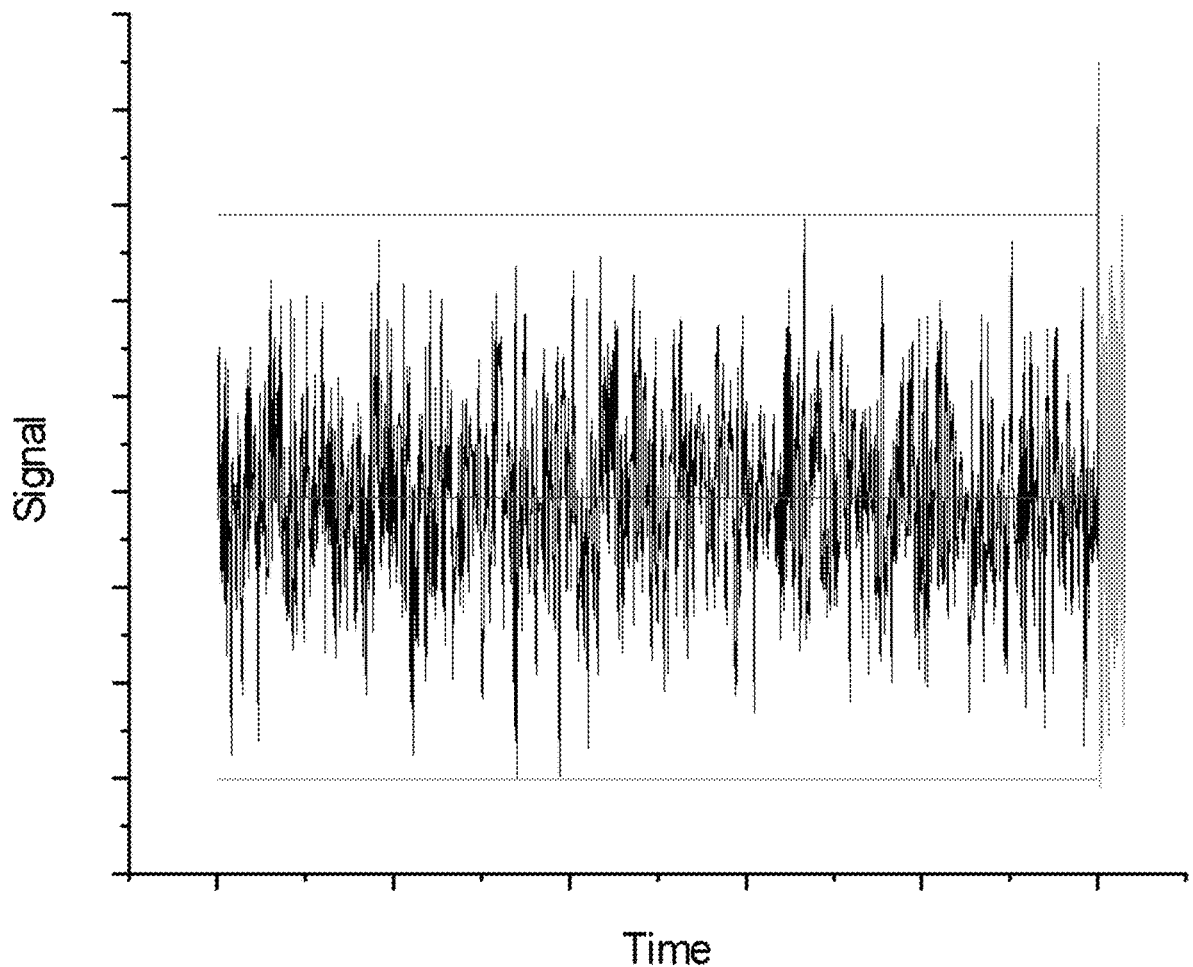
FIG. 12 illustrates a graphical representation of data collected over time with a single outlier data point.
Figure 13:
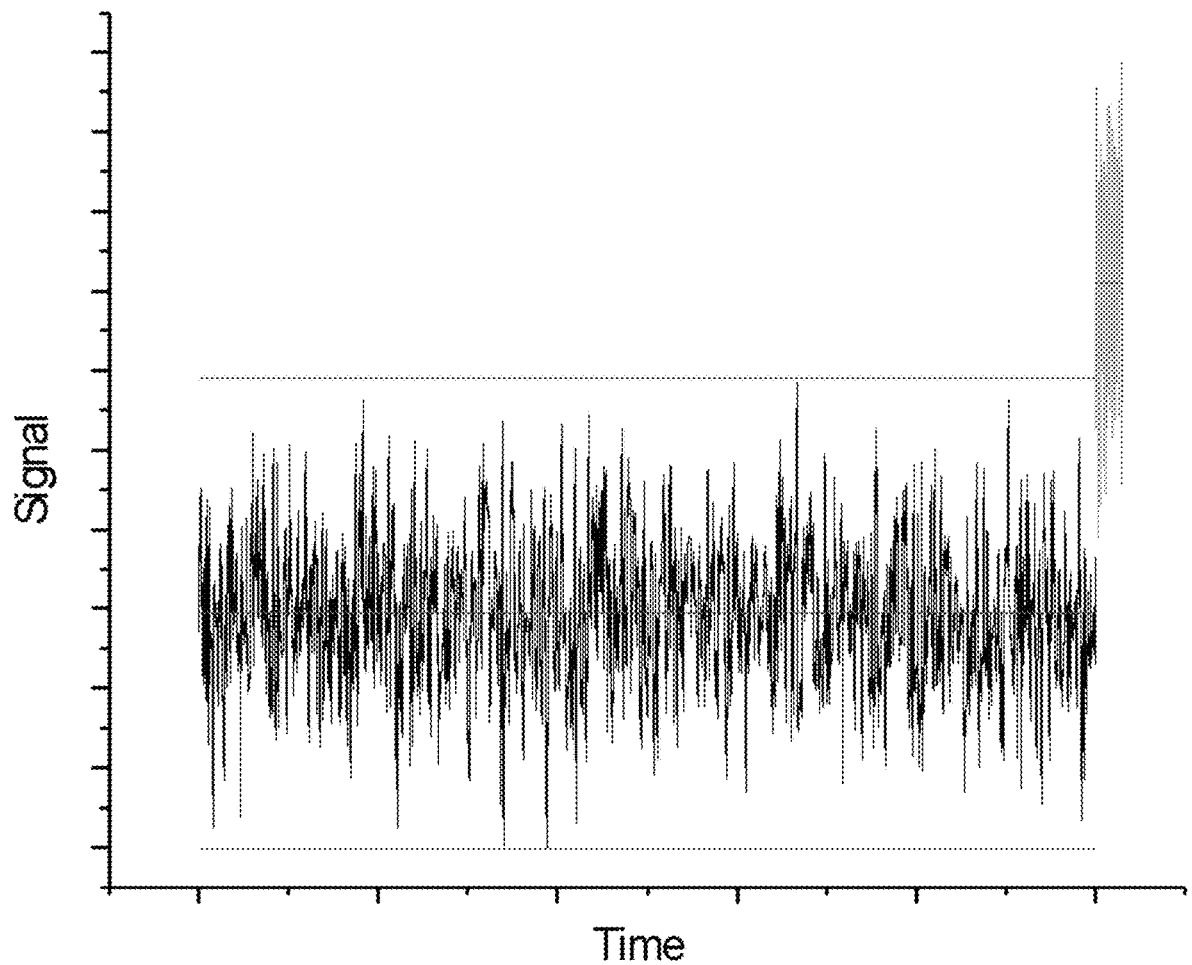
FIG. 13 illustrates a graphical representation of data collected over time which shows sudden change with the calculated mean above the expected mean +3σ at the normal state.
Figure 14:
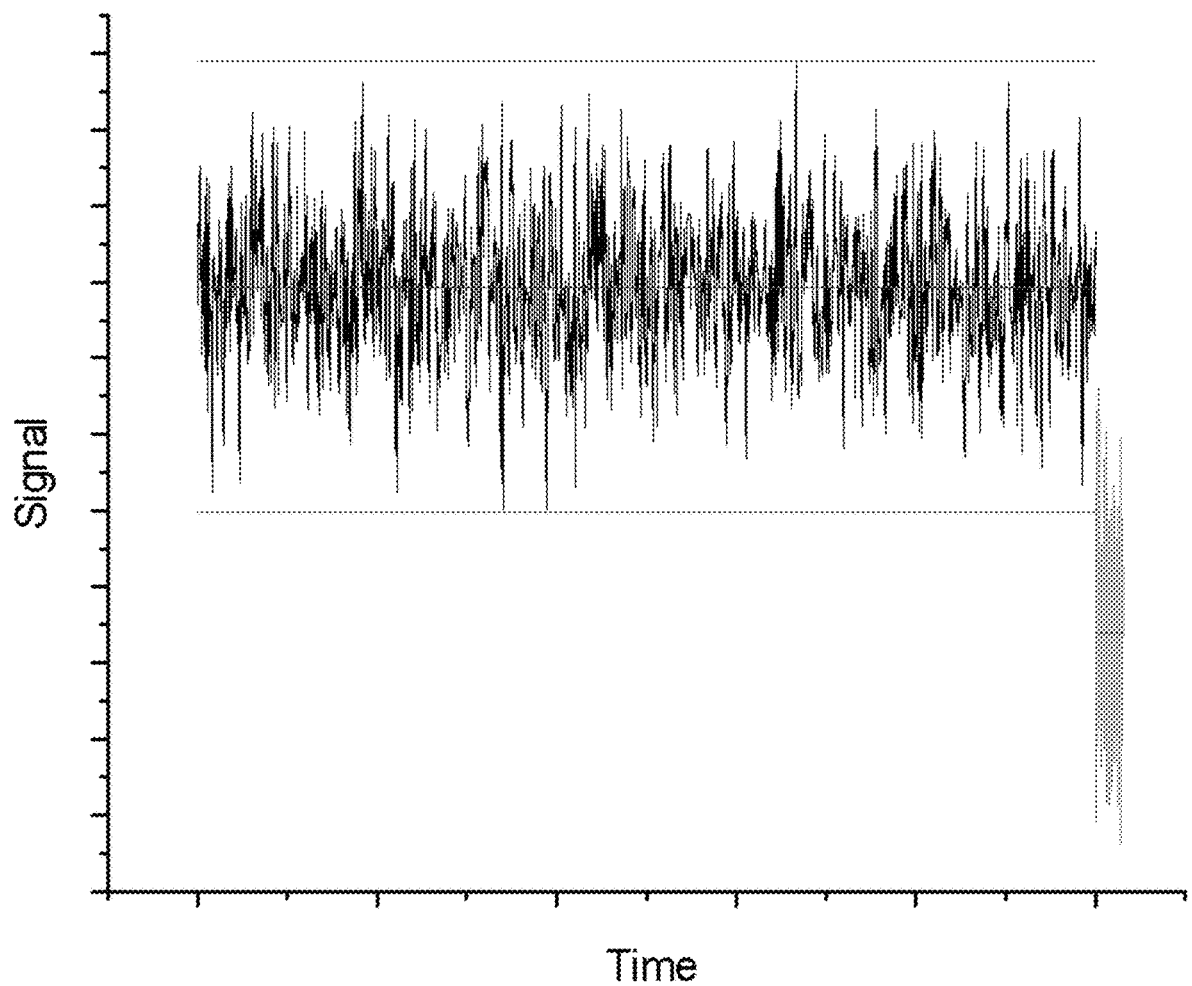
FIG. 14 illustrates a graphical representation of data input over time which shows sudden change with the calculated mean is below the expected mean −3σ at the normal state.

In a further variant, referring to FIGS. 12-14, graphical representations of data monitoring illustrate what occurs when an abnormal change is detected. The black line in FIGS. 12-14 represents the measured signal when the user is in a normal healthy condition. The red line represents the expected mean, based on the normal data measurements of the user for a particular physical state. The green lines represent the expected mean +3σ (3 standard deviations) and expected mean −3σ, respectively. Referring to FIG. 12, the device detects a singular data point (magenta line) above the expected mean +3σ and thus triggers measurements at a higher repetition rate. However, further measurements (cyan line) illustrate that no real changes occur in the user's physiology and thus confirm that the singular measurement is an outlier. Referring to FIG. 13, the subsequent measurements (cyan line) illustrate that the mean is significantly above expected mean +3σ. Thus the user in this situation experiences real changes between the left and right side of his body and the alarm is triggered. Referring to FIG. 14, the subsequent measurements (cyan line) illustrate that the mean is significantly below expected mean −3σ. Thus, in this situation the user also experiences real changes between the left and right side of his body and the alarm is triggered.

What is claimed is:

1. A wearable device for monitoring muscle tension and other physiological data of a first user, comprising:
   a communication interface configured to connect the wearable device to other devices via wireless or wired communication;
   at least one band adapted to fit one or more human limbs of the first user, wherein the at least one band comprises a plurality of sensors configured to obtain measurements of the first user from the one or more human limbs of the first user, wherein the measurements of the first user comprise at least one of: muscle tension data, physiological data, and motion data;
   processing circuitry configured to receive at least one of muscle tension data, physiological data, and motion data from the plurality of sensors, wherein the processing circuitry implements: (i) discriminant analysis on the received at least one of the muscle tension data, the physiological data, and the motion data from the plurality of sensors, (ii) decision tree logic on the received at least one of the muscle tension data, the physiological data, and the motion data from the plurality of sensors, and (iii) filtering methods and state estimations on the received at least one of the muscle tension data, the physiological data, and the motion data from the plurality of sensors, thereby generating statistical models for the first user, wherein the statistical models are based on at least one of the discriminant analysis, the decision tree logic, and the filtering methods and the state estimations;
   an alarm component connected to the processing circuitry;
   transmitter circuitry configured to transmit the measurements of the first user to an external device in use by a second user, wherein the external device is configured to take measurements of the second user; and
   a rechargeable battery configured to power the wearable device in use by the first user;
   wherein the statistical models are receiving a threshold, wherein the statistical models are employed by the processing circuitry for classifying a first physical state of the first user, identifying changes in the measurements of the first user, classifying a second physical state of the first user in response to identifying the changes in the measurements of the first user, calculating differences between the measurements of the first user and measurements of the second user, comparing the threshold to the calculated differences, and triggering the alarm component if the calculated differences is above the threshold;
   wherein the identified changes in the first user correspond to the differences in the measurements of the first user, and
   wherein the plurality of sensors comprises electromyography, muscle contraction sensors, motion detectors, and physiological sensors.

2. The device of claim 1, wherein the physiological sensors obtain the physiological data of the first user, wherein the physiological data is blood pressure, heart rate, and vein pulse wave data.

3. The device of claim 1, wherein the one or more human limbs are different limbs of the first user on which the measurements of first user are obtained.

4. The device of claim 1, wherein the processing circuitry is configured to compare the data from each sensor of the plurality of sensors to the statistical models generated for each physical state of the first user.

5. The device of claim 1, wherein the external device comprises a wearable device in use by the second user, an external interface, internet, and a medical care facility network.

6. The device of claim 5, wherein the wearable device in use by the second user is configured to obtain measurements from the second user and receive measurements from the wearable device in use by the first user, thereby: comparing the measurements from the wearable device in use by the first user to the measurements obtained from the wearable device in use by the second user.

7. The device of claim 1, wherein the threshold is continuously updated by incorporating newly calculated differences of muscle tension data.

8. The device of claim 1, wherein the changes in the first user are continuous or non-continuous.

9. The device of claim 1, wherein the transmitter circuitry is configured to transmit sound alerts to the external device.

10. The device of claim 1, wherein the processing circuitry is configured to continuously update the statistical models with newly received data from the plurality of sensors.

11. The device of claim 1, wherein each sensor of the plurality of sensors is configured to increase a sampling rate for the measurements of the first user when the processing circuitry detects the differences in the measurements of the first user are above the threshold.

12. The device of claim 1, further comprising: an energy-harvesting circuitry configured to convert energy from an environment of the wearable device to charge the rechargeable battery.

13. A method for monitoring muscle tension and other physiological data of a first user, comprising:
   placing a wearable device on one or more human limbs of the first user, wherein the wearable device comprises at least one band adapted to fit the one or more human limbs of the first user, wherein the at least one band comprise a plurality of sensors configured to obtain measurements of the first user from the one or more human limbs of the first user, wherein the measurements of the first user comprise at least one of: muscle tension data, physiological data, and motion data;
   receiving at least one of muscle tension data, physiological data, and motion data from the plurality of sensors;
   transmitting the measurements of the first user to an external device in use by a second user, wherein the external device is configured to take measurements of the second user;
   implementing (i) discriminant analysis on the received at least one of the muscle tension data, the physiological data, and the motion data from the plurality of sensors, (ii) decision tree logic on the received at least one of the muscle tension data, the physiological data, and the motion data from the plurality of sensors, and (iii) filtering methods and state estimations on the received at least one of muscle tension data, physiological data, and motion data from the plurality of sensors, thereby generating statistical models for the first user, wherein the statistical models are based on at least one of the discriminant analysis, the decision tree logic, and the filtering methods and the state estimations;
   classifying a first physical state of the first user by the statistical models;
   identifying changes in the first user by the statistical models;

classifying a second physical state of the user in response to identifying changes in the first user by the statistical models;
calculating differences between the measurements of the first user and measurements of the second user;
comparing a threshold to differences in the measurements of the first user by the statistical models;
triggering an alarm component if the calculated differences is above the threshold;
wherein the identified changes in the first user correspond to the differences in the measurements of the first user.

14. The method of claim 13, wherein the physiological data of the user is blood pressure, heart rate, and vein pulse wave data.

15. The method of claim 13, wherein the one or more human limbs are different limbs of the first user on which the measurements of first user are obtained.

16. The method of claim 13, further comprising continuously updating the statistical models with newly received data.

17. The method of claim 13, further comprising wearing a first band on a first limb and a second band on a second limb.

18. The method of claim 13, wherein the external device comprises a wearable device in use by the second user, an external interface, internet, and a medical care facility network.

19. The method of claim 18, further comprising:
obtaining measurements from the wearable device in use by the second user,
receiving measurements from the wearable device in use by the second user; and
comparing the measurements from the wearable device in use by the first user to the measurements obtained from the wearable device in use by the second user.

20. The method of claim 13, wherein each sensor of the plurality of sensors is configured to increase a sampling rate for the measurements of the first user when the processing circuitry detects the differences in the measurements of the first user are above the threshold.

* * * * *